United States Patent [19]

Fujishima

[11] Patent Number: 5,278,182
[45] Date of Patent: Jan. 11, 1994

[54] AZOLE-1-CARBOXYLIC ACID ESTER DERIVATIVES AND FUNGICIDAL COMPOSITIONS

[75] Inventor: Hiroshi Fujishima, Tokushima, Japan

[73] Assignee: Otsuka Kagaku Kabushiki Kaisha, Osaka, Japan

[21] Appl. No.: 979,334

[22] Filed: Nov. 20, 1992

[30] Foreign Application Priority Data

Nov. 22, 1991 [JP] Japan .................. 3-307559

[51] Int. Cl.$^5$ .................. A01N 43/50; A01N 43/653; C07D 233/22; C07D 249/12
[52] U.S. Cl. .................. 514/399; 514/383; 548/266.8; 548/344.1
[58] Field of Search .......... 548/334.1, 266.8; 514/383, 399

[56] References Cited

U.S. PATENT DOCUMENTS

| | | | |
|---|---|---|---|
| 4,078,139 | 3/1978 | Barton et al. | 548/334.1 X |
| 4,746,673 | 5/1988 | Imai et al. | 548/334.1 X |
| 4,879,388 | 11/1989 | Quan et al. | 548/266.8 X |

FOREIGN PATENT DOCUMENTS 62-238272 10/1987 Japan .................. 548/334.1

*Primary Examiner*—Mary C. Lee
*Assistant Examiner*—Fiona T. Powers
*Attorney, Agent, or Firm*—Armstrong, Westerman, Hattori, McLeland & Naughton

[57] ABSTRACT

Disclosed is a azole-1-carboxylic acid ester derivative represented by the general formula

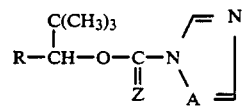

wherein R is a lower alkyl, halo-lower alkyl, lower alkenyl or halo-lower alkenyl group, A is =N— or =CH—, and Z is an oxygen or sulfur atom. The azole-1-carboxylic acid ester derivative has fungicidal activity.

2 Claims, No Drawings

AZOLE-1-CARBOXYLIC ACID ESTER DERIVATIVES AND FUNGICIDAL COMPOSITIONS

This invention relates to azole-1-carboxylic acid ester derivatives and fungicidal compositions containing said derivatives.

Among known compounds analogous in structure to the azole-1-carboxylic acid ester derivatives of this invention, there is imidazole-1-carboxylic acid benzyl ester [cf. The Journal of Organic Chemistry, 47 (23), 4471–4477], for instance. However, said compound has no fungicidal activity at all.

On the other hand, Japanese Kokai Patent Publication No. 281867/1987 discloses azole-1-carboxylic acid ester derivatives having fungicidal activity, for example imidazole-1-carboxylic acid 1'-(p-chlorophenoxy)-3',3'-dimethyl-2'-butyl ester and 1'-(p-chlorophenyl)-3',3'-dimethyl-2'-butyl ester, with the corresponding fungicidal activity data. However, these compounds are not fully satisfactory in fungicidal activity. Moreover, they are phytotoxic.

The azole-1-carboxylic acid ester derivatives of this invention are novel compounds not yet described in the literature and have the following general formula (1).

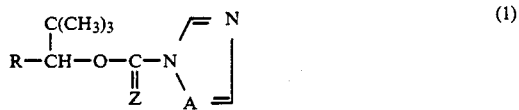

wherein R is a lower alkyl, halo-lower alkyl, lower alkenyl or halo-lower alkenyl group, A is =N— or =CH—, and Z is an oxygen or sulfur atom.

As used in the present specification, the term "lower alkyl group" includes alkyl groups containing 1 to 6 carbon atoms, such as methyl, ethyl, n-propyl, isopropyl, n-butyl, isobutyl, tert-butyl, n-hexyl, methylbutyl, isopentyl, etc., "halo-lower alkyl group" includes halo-substituted alkyl groups containing 1 to 4 carbon atoms, such as chloromethyl, bromomethyl, fluoromethyl, dichloromethyl, difluoromethyl, trifluoromethyl, chloroethyl, bromoethyl, fluoroethyl, chloropropyl, bromopropyl, dichloropropyl, bromobutyl, chlorobutyl, dichlorobutyl, etc., "lower akenyl group" includes alkenyl groups containing 2 to 4 carbon atoms, such as vinyl, propenyl, butenyl, etc., and "halo-lower alkenyl group" includes halo-substituted alkenyl groups containing 2 to 4 carbon atoms, such as chlorovinyl, dichlorovinyl, bromovinyl, fluorovinyl, chloropropenyl, bromopropenyl, chlorobutenyl and so on.

The compounds of the formula (1) according to the invention are useful as agricultural and horticultural insecticides. The compounds of the invention are volatile and thus can be used for various applications of sterilization, e.g. as a soil fungicide.

The compounds of this invention can be produced according to the following reaction schemas.

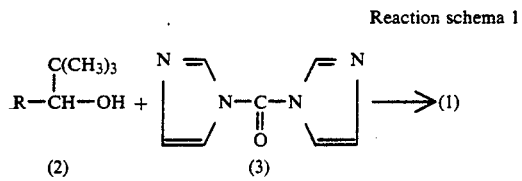

Reaction schema 1

(R being as defined above)

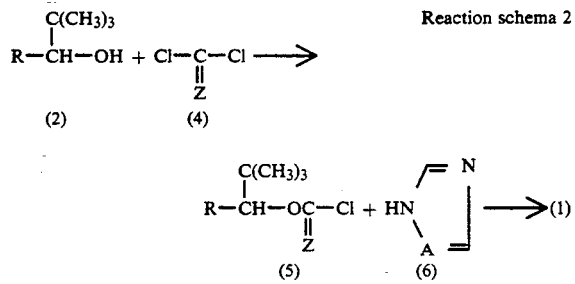

(R, A and Z being as defined above)

According to the reaction schema 1, the compounds of this invention are produced by reacting a carbinol of general formula (2) with N,N'-carbonyldiimidazole of formula (3). This reaction is carried out without using any solvent or in an appropriate solvent. As the solvent to be used, there may be mentioned ethers such as diethyl ether, dibutyl ether, tetrahydrofuran, dioxane, etc., halogenated hydrocarbons such as methylene chloride, chloroform, dichloroethane, ketones such as acetone, methyl ethyl ketone, methyl isopropyl ketone, cyclohexanone, etc., aromatic hydrocarbons such as benzene, toluene, xylene, etc., ethyl acetate, dimethylformamide, acetonitrile, dimethyl sulfoxide, etc., and mixtures of these solvents, among others. The quantitive ratio between the compound of general formula (2) and the compound of formula (3) is not critical but it is recommended, generally, that the latter be used in a proportion of about 0.5 to 2 moles, preferably about 0.7 to 1.5 moles, per mole of the former. The reaction may be carried out either under cooling or under warming. Generally, however, the reaction proceeds smoothly at a temperature from room temperature to the neighborhood of the boiling point of the solvent employed. The reaction time is generally about 1 to 10 hours.

According to the reaction schema 2, the compounds of this invention are produced by reacting a carbinol of general formula (2) with a compound of general formula (4) and then reacting the resulting compound of general formula (5) with imidazole or triazole. This series of reactions can be carried out without using any solvent or in an appropriate solvent. As the solvent which can be used here, there may be mentioned ethers such as diethyl ether, dibutyl ether, tetrahydrofuran, dioxane, etc., halogenated hydrocarbons such as methylene chloride, chloroform, dichloroethane, etc., ketones such as acetone, methyl ethyl ketone, methyl isopropyl ketone, cyclohexanone, etc., aromatic hydrocarbons such as benzene, toluene, xylene, etc., ethyl acetate, dimethylformamide, acetonitrile, dimethyl sulfoxide, and mixtures of these solvents, among others. In carrying out the reaction between the compound of general formula (2) and the compound of general formula (4), it is recommendable that the compound of general formula (4), either in a gaseous form or a liquid form, be introduced into the reaction system or a solution of the compound of general formula (4) in such a solvent as mentioned above be added dropwise to the reaction system. In the practice of the invention, a compound capable of generating the compound of general formula (4) may be used in lieu of the latter compound. As such compound, any compound known in the art that is capable of generating the compound of general formula (4) under the reaction conditions can be used. Trichloromethyl chloroformate is an example. The quantitative ratio between the compound of general formula (2) and the compound of general formula (4) is not critical but, generally, the latter is used preferably in a proportion of about 0.5 to 5 moles, preferably about 1 to 3 moles, per mole of the former. It is preferable that a basic compound be present in the reaction system. The basic compound may be any compound known in the art that is capable of capturing the hydrogen chloride formed in the course of the reaction. Examples are triethylamine, tributylamine, dimethylaniline and pyridines. Such basic compound is used generally in a proportion of about 0.5 to 5 moles, preferably about 1 to 3 moles, per mole of the compound of general formula (2). The reaction may be carried out at room temperature or under cooling. Generally, the reaction proceeds smoothly at about $-10°$ C. to room temperature, and the reaction time required is about 1 to 15 hours. The thus-formed compound of general formula (5) is submitted to the next reaction in an isolated form or as it is present in the reaction mixture.

In carrying out the reaction between the compound of general formula (5) as produced by the above reaction and imidazole or triazole, the quantitative ratio therebetween is not critical but, generally, the latter is used preferably in a proportion of about 0.5 to 2 moles, preferably about 0.7 to 1.5 moles, per mole of the former. It is preferable that a basic compound such as one mentioned above be present in this reaction system as well. It is generally recommendable that the basic compound be used in a proportion of about 0.5 to 2 moles, preferably about 0.7 to 1.5 moles, per mole of the compound of general formula (5). The reaction may be conducted under cooling or under warming but, generally, the reaction proceeds smoothly at a temperature from room temperature up to the vicinity of the boiling point of the solvent employed. The reaction time is generally about 1 to 10 hours.

The compound of general formula (2) to be used as the starting material in accordance with the above reaction schemas 1 and 2 can readily be prepared by a per se known method, for example by the methods illustrated below by way of reaction schemas 3 and 4 [cf. Synthesis, 18 (1977) and Journal of the American Chemical Society, 71, 122 (1949)].

R—MgX+(CH$_3$)$_3$CHO→(2)  Reaction Schema 3

(R being as defined above and X being a halogen atom)

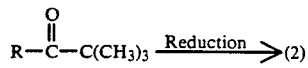

Reaction schema 4

(R being as defined above)

The compounds of this invention as produced in the above manner can be isolated and purified from the respective reaction mixtures by ordinary separation means, for example by solvent extraction, solvent dilution, recrystallization, column chromatography, etc., to give the compounds of the invention with high purity.

The compounds of this invention are characterized by their potent fungicidal activity and broad fungicidal activity spectrum. They exhibit excellent fungicidal activity against various pathogenic fungi causing powdery mildew, scab, smut, gray mold, anthracnose, blast, Helminthosporium leaf spot, sheath blight, downy mildew, Phytophthora rot and so on. Furthermore, the compounds of this invention, when used at concentrations necessary and sufficient to control such pathogenic fungi, will neither exhibit phytotoxicity to crop plants nor toxicity to warm-blooded animals. Therefore, the compounds of this invention can be used effectively in controlling diseases of various vegetables, fruit trees, and rice and other crop plants.

In applying the compounds of the invention as fungicides, said compounds as such may be applied but, generally, they are used in admixture with the auxiliaries commonly used in agrochemical formulations. The fungicidal compositions of this invention are not limited to any particular application form but may advantageously be provided in such forms as dusts, emulsifiable concentrates, wettable powders, flowable formulations and granules. Those auxiliaries which are commonly used in the art can be liberally selected and used. Thus, for example, dust diluents such as diatomaceous earth, kaolin, clay, bentonite, white carbon, talc, etc., surfactants such as polyoxyethylene alkyl ethers, polyoxyethylene alkylphenyl ethers, polyoxyethylene sorbitan fatty acid esters, polyoxyethylene fatty acid esters, alkylbenzenesulfonic acid sodium salts, sodium ligninsulfonate, sodium alkyl sulfates, sodium polyoxyethylene alkyl sulfates, salts of naphthalenesulfonic acid-formaldehyde condensates, etc., and organic solvents such as benzene, toluene, xylene, acetone, cyclohexanone, methanol, ethanol, dioxane, dimethylformamide, etc. can be employed.

The proportion of the compound of the invention in various fungicidal compositions of the invention is not critical and may range from about 0.1 to 90% by weight, preferably about 1 to 70% by weight, the balance being auxiliary agents such as those mentioned above.

In applying any fungicidal formulation of the invention, it may be dusted or otherwise applied either as such without dilution or after about 500- to 10,000-fold dilution. The proper application rate may vary depending on the specific form of composition, the method of application, the season or time of application, the disease to be controlled and other factors and, hence, cannot be specified in general terms. Roughly speaking, however, the compositions are preferably applied at the rate of about 10 to 200 g/10 ares as the active ingredient.

The following production examples, formulation examples and test examples are further illustrative of the present invention.

PRODUCTION EXAMPLE 1

Production of (2,2-dimethyl-3-heptoxycarbonyl)-1-imidazole

To 20 ml of a solution of 1.4 g (10 mmol) of 2,2'-dimethyl-3-heptanol in ethyl acetate was added 2.4 g (15 mmol) of N,N'-carbonyldiimidazole, and the mixture was stirred at 60° C. for 5 hours. The reaction mixture was subjected to post-treatment in the conventional manner, and the residue obtained was purified by silica gel column chromatography to give 1.7 g of the title compound.

Colorless oil $^1$H-NMR (CDCl$_3$) δppm: 1.00 (9H), 0.8-1.8 (9H), 4.81 (1H), 7.05 (1H), 7.43 (1H), 8.15 (1H).

PRODUCTION EXAMPLE 2

Production of (1-bromo-3,3-dimethyl-2-butoxycarbonyl)-1-imidazole

To 50 ml of a solution of 1.8 g (10 mmol) of 1-bromo-3,3-dimethyl-2-butanol in ethyl acetate was added 0.7 g (11 mmol) of pyridine. The solution was cooled to 0° C., and 5 ml of a solution of 0.9 g (5 mmol) of trichloromethyl chloroformate in ethyl acetate was added dropwise. The resultant mixture was stirred overnight at room temperature and then cooled to 0° C. on an ice bath. Then, 0.7 g (10 mmol) of imidazole and 0.7 g (11 mmol) of pyridine were added, and the resultant mixture was stirred for 2 hours. After post-treatment, which was performed in the conventional manner, the residue was purified by silica gel column chromatography to give 2.1 g of the title compound.

Melting point: 53°-54° C.

$^1$H-NMR (CDCl$_3$) δppm: 1.03 (9H), 3.49-3.72 (2H), 5.15 (1H), 7.09 (1H), 7.45 (1H), 8.17 (1H).

By proceeding in the same manner as in Production Example 1 or 2, the compounds given below in Table 1 were obtained. Their physical properties and $^1$H-NMR spectrum data are also shown in Table 1.

TABLE 1

| Cmpd. No. | Structure | Physical property | NMR spectrum (CDCl$_3$) δppm |
|---|---|---|---|
| 3 | CH$_3$—CH(—O—C(=O)—N-imidazolyl)—C(CH$_3$)$_3$ | mp. 43–44° C. | 1.00(9H), 1.32(3H), 4.75(1H), 7.00(1H), 7.35(1H), 8.05(1H) |
| 4 | C$_2$H$_5$—CH(—O—C(=O)—N-imidazolyl)—C(CH$_3$)$_3$ | mp. 62–63° C. | 1.01(12H), 1.72(2H), 4.82(1H), 7.10(1H), 7.51(1H), 8.21(1H) |
| 5 | n-C$_3$H$_7$—CH(—O—C(=O)—N-imidazolyl)—C(CH$_3$)$_3$ | mp. 75–76° C. | 0.90~1.5(7H), 1.00(9H), 4.72(1H), 7.05(1H), 7.38(1H), 8.04(1H) |
| 6 | iso-C$_3$H$_7$—CH(—O—C(=O)—N-imidazolyl)—C(CH$_3$)$_3$ | mp. 76–77° C. | 0.97(9H), 1.02(6H), 2.0~2.40(1H), 4.72(1H), 7.04(1H), 7.38(1H), 8.08(1H) |
| 7 | n-C$_4$H$_9$—CH(—O—C(=S)—N-imidazolyl)—C(CH$_3$)$_3$ | oily | 1.02(9H), 0.8~1.9(9H), 5.11(1H), 7.11(1H), 7.52(1H), 8.21(1H) |
| 8 | n-C$_6$H$_{13}$—CH(—O—C(=O)—N-imidazolyl)—C(CH$_3$)$_3$ | mp. 45–47° C. | 0.8~1.91(11H), 1.01(9H), 4.80(1H), 7.05(1H), 7.41(1H), 8.15(1H) |
| 9 | n-C$_3$H$_7$—CH(CH$_3$)—CH(—O—C(=O)—N-imidazolyl)—C(CH$_3$)$_3$ | oily | 0.92(3H), 1.01(9H), 0.8-2.11(8H), 4.80(1H), 7.05(1H), 7.42(1H), 8.12(1H) |
| 10 | C$_2$H$_5$—CH(CH$_3$)—CH$_2$—CH(—O—C(=O)—N-imidazolyl)—C(CH$_3$)$_3$ | oily | 1.00(12H), 0.91-1.89(8H), 4.82(1H), 7.01(1H), 7.42(1H), 8.10(1H) |
| 11 | (CH$_3$)$_2$CH—(CH$_2$)$_3$—CH(—O—C(=O)—N-imidazolyl)—C(CH$_3$)$_3$ | mp. 71–73° C. | 0.86(6H), 0.97(9H), 1.2~2.0(7H), 4.80(1H), 7.05(1H), 7.40(1H), 8.10(1H) |
| 12 | H$_2$C=CH—CH$_2$—CH(—O—C(=O)—N-imidazolyl)—C(CH$_3$)$_3$ | oily | 1.00(9H), 2.21~2.50(2H), 4.71~5.15(3H), 5.35~5.91(1H), 7.04(1H), 7.42(1H), 8.03(1H) |

TABLE 1-continued

| Cmpd. No. | Structure | Physical property | NMR spectrum (CDCl$_3$) δppm |
|---|---|---|---|
| 13 | CH$_3$—CH=CH—CH(—C(CH$_3$)$_3$)—O—C(=O)—N(pyrazole) | oily | 1.00(9H), 1.81(3H), 5.40~6.02(3H), 7.01(1H), 7.32(1H), 8.05(1H) |
| 14 | CH$_2$=C(CH$_3$)—CH(—C(CH$_3$)$_3$)—O—C(=O)—N(pyrazole) | mp. 77–78° C. | 1.00(9H), 1.84(3H), 4.90~5.21(3H), 7.12(1H), 7.55(1H), 8.23(1H) |
| 15 | CH$_3$CH=CH—CH$_2$—CH(—C(CH$_3$)$_3$)—O—C(=O)—N(pyrazole) | mp. 63–64° C. | 1.01(9H), 1.87(3H), 2.85~2.96(1H), 4.90~5.14(1H), 5.83~6.15(1H), 7.10(1H), 7.34(1H), 8.11(1H) |
| 16 | H$_2$C=CH—CH$_2$CH$_2$CH(—C(CH$_3$)$_3$)—O—C(=O)—N(pyrazole) | oily | 1.03(9H), 1.41~2.30(5H), 4.70~5.11(2H), 5.41~5.95(1H), 7.05(1H), 7.44(1H), 8.11(1H) |
| 17 | Cl—CH$_2$—CH(—C(CH$_3$)$_3$)—O—C(=O)—N(pyrazole) | oily | 1.01(9H), 3.52(2H), 5.2(1H), 7.10(1H), 7.50(1H), 8.15(1H) |
| 18 | Cl$_2$CH—CH(—C(CH$_3$)$_3$)—O—C(=O)—N(pyrazole) | mp. 82–83° C. | 1.10(9H), 5.15(1H), 6.05(1H), 7.05(1H), 7.25(1H), 8.11(1H) |
| 19 | Br—CH$_2$—CH(—C(CH$_3$)$_3$)—O—C(=O)—N(pyrazole) | oily | 1.05(9H), 3.50~3.80(2H), 5.50(1H), 7.12(1H), 7.52(1H), 8.22(1H) |
| 20 | Br—CH$_2$—CH$_2$—CH(—C(CH$_3$)$_3$)—O—C(=O)—N(pyrazole) | oily | 1.01(9H), 1.80~2.37(4H), 4.95(1H), 7.05(1H), 7.25(1H), 8.07(1H) |
| 21 | Br—(CH$_2$)$_3$—CH(—C(CH$_3$)$_3$)—O—C(=O)—N(pyrazole) | oily | 1.00(9H), 2.18~2.51(2H), 4.67~5.23(4H), 5.44~6.05(1H), 7.05(1H), 7.50(1H), 8.11(1H) |
| 22 | Br—(CH$_2$)$_4$—CH(—C(CH$_3$)$_3$)—O—C(=O)—N(pyrazole) | oily | 0.95(9H), 1.21~1.85(8H), 4.95(1H), 7.05(1H), 7.21(1H), 8.05(1H) |
| 23 | Br—CH$_2$—CH(—C(CH$_3$)$_3$)—O—C(=O)—N(pyrazole) | oily | 1.02(9H), 3.85(2H), 5.24(1H), 8.05(1H), 8.85(1H) |

| Formulation Example 1 | |
|---|---|
| Ingredient | Weight parts |
| Compound of the invention | 25 |
| White carbon | 45 |
| Diatomaceous earth | 16 |
| Sodium higher alcohol sulfate | 2 |
| Sodium salt of β-naphthalenesulfonic acid-formaldehyde condensate | 2 |
| Alkylphenylphenol sulfate salt | 10 |
| Total | 100 |

The above ingredients were thoroughly blended using a mixer and then finely ground in a pulverizing mill to give a 25% wettable powder.

| Formulation Example 2 | |
| --- | --- |
| Ingredient | Weight parts |
| Compound of the invention | 20 |
| Polyoxyethylene styrylphenyl ether | 8 |
| Sodium dodecylbenzenesulfonate | 4 |
| Xylene | 68 |
| Total | 100 |

The above ingredients were mixed and stirred to give a 20% emulsifiable concentrate.

TEST EXAMPLE 1

PREVENTIVE EFFECT ON CUCUMBER POWDERY MILDEW

The wettable powder prepared in Formulation Example 1 was diluted to a concentration of 100 or 500 ppm and applied, by spraying, to cucumber seedings cultivated in pots (7.5 cm in diameter, 200 ml in capacity). After air-drying, the seedlings were spray-inoculated with a spore suspension of *Sphaerotheca fuliginea* (pathogen of cucumber powdery mildew). Two weeks later, the percentage lesion area was determined and the control index was calculated by the formula shown below.

control index (%) = [(the percentage lesion area of untreated portion − the percentage lesion area of treated portion)/the percentage lesion area of untreated portion] × 100

The seedlings were also examined for signs of phytotoxicity.

The results thus obtained are shown below in Table 2.

TABLE 2

| | Control index | | Phyto- |
| --- | --- | --- | --- |
| Compound No. | 100 ppm | 500 ppm | toxicity |
| 1 | 83 | 100 | None |
| 2 | 100 | 100 | None |
| 3 | 81 | 92 | None |
| 4 | 70 | 87 | None |
| 5 | 100 | 100 | None |
| 6 | 88 | 100 | None |
| 7 | 81 | 100 | None |
| 8 | 70 | 85 | None |
| 9 | 85 | 100 | None |
| 10 | 100 | 100 | None |
| 11 | 100 | 100 | None |
| 12 | 78 | 94 | None |
| 13 | 100 | 100 | None |
| 14 | 87 | 100 | None |
| 15 | 83 | 96 | None |
| 16 | 81 | 96 | None |
| 17 | 100 | 100 | None |
| 18 | 100 | 100 | None |
| 19 | 80 | 100 | None |
| 20 | 73 | 95 | None |
| 21 | 85 | 97 | None |
| 22 | 93 | 100 | None |
| 23 | 95 | 100 | None |

TEST EXAMPLE 2

Preventive Effect on Cucumber Gray Mold

The wettable powder prepared in Formulation Example 1 was diluted to a concentration of 100 ppm or 500 ppm and applied, by spraying, to cucumber seedlings cultivated in pots (7.5 cm in diameter, 200 ml in capacity). After air-drying, the seedlings were sprayinoculated with a suspension of spores of *Botrytis cinerea* (pathogen). Seven days later, the percentage lesion area was determined and the control index was calculated as in Text Example 1.

The results obtained are shown in Table 3.

TABLE 3

| | Control index | | Phyto- |
| --- | --- | --- | --- |
| Compound No. | 100 ppm | 500 ppm | toxicity |
| 1 | 88 | 100 | None |
| 2 | 100 | 100 | None |
| 3 | 71 | 83 | None |
| 4 | 89 | 100 | None |
| 5 | 100 | 100 | None |
| 6 | 84 | 97 | None |
| 7 | 77 | 80 | None |
| 8 | 83 | 98 | None |
| 9 | 89 | 100 | None |
| 10 | 100 | 100 | None |
| 11 | 90 | 100 | None |
| 12 | 84 | 100 | None |
| 13 | 100 | 100 | None |
| 14 | 100 | 100 | None |
| 15 | 93 | 100 | None |
| 16 | 72 | 84 | None |
| 17 | 100 | 100 | None |
| 18 | 100 | 100 | None |
| 19 | 93 | 100 | None |
| 20 | 81 | 100 | None |
| 21 | 91 | 100 | None |
| 22 | 88 | 100 | None |
| 23 | 96 | 100 | None |

TEST EXAMPLE 3

Preventive Effect on Cucumber Phytophthora Rot

The wettable powder prepared in Formulation Example 1 was diluted to a concentration of 100 ppm or 500 ppm and applied, by spraying, to cucumber seedlings cultivated in pots (7.5 cm in diameter, 200 ml in capacity). After air-drying, the seedlings were spray-inoculated with a suspension of zoospores of *Phytophthora parasitica*. Five days later, the percentage lesion area was determined and the control index was calculated as in Test Example 1.

The results obtained are shown in Table 4.

TABLE 4

| | Control index | | Phyto- |
| --- | --- | --- | --- |
| Compound No. | 100 ppm | 500 ppm | toxicity |
| 1 | 84 | 94 | None |
| 2 | 100 | 100 | None |
| 3 | 82 | 96 | None |
| 4 | 94 | 100 | None |
| 5 | 100 | 100 | None |
| 6 | 90 | 100 | None |
| 7 | 70 | 81 | None |
| 8 | 85 | 94 | None |
| 9 | 80 | 89 | None |
| 10 | 100 | 100 | None |
| 11 | 84 | 100 | None |
| 12 | 91 | 100 | None |
| 13 | 100 | 100 | None |
| 14 | 100 | 100 | None |
| 15 | 81 | 87 | None |
| 16 | 73 | 80 | None |
| 17 | 100 | 100 | None |
| 18 | 100 | 100 | None |
| 19 | 88 | 93 | None |
| 20 | 80 | 92 | None |
| 21 | 83 | 93 | None |
| 22 | 92 | 100 | None |

TABLE 4-continued

| Compound No. | Control index 100 ppm | 500 ppm | Phyto-toxicity |
| --- | --- | --- | --- |
| 23 | 95 | 100 | None |

What is claimed is:

1. An azole-1-carboxylic acid ester compound of the formula

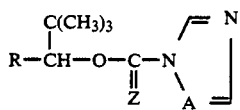

wherein R is a lower alkyl, halo-lower alkyl, lower alkenyl or halo-lower alkenyl group, A is =CH—, and Z is an oxygen or sulfur atom.

2. A fungicidal composition comprising an azole-1-carboxylic acid ester compound of the formula

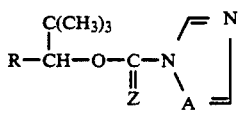

wherein R is a lower alkenyl, halo-lower alkyl, lower alkenyl or halo-alkenyl group, A is =CH—, and Z is an oxygen or sulfur atom; and a carrier therefor.

* * * * *